(12) United States Patent
Yankielun

(10) Patent No.: US 6,281,688 B1
(45) Date of Patent: Aug. 28, 2001

(54) TRANSMISSION LINE REFLECTOMETER USING FREQUENCY-MODULATED CONTINUOUS WAVE

(75) Inventor: Norbert E. Yankielun, Lebanon, NH (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 09/104,268

(22) Filed: Jun. 25, 1998

(51) Int. Cl.[7] ................................................ G01R 27/04
(52) U.S. Cl. ......................... 324/643; 324/642; 324/632
(58) Field of Search .................................. 342/122, 123, 342/124, 128; 324/643, 632, 642

(56) References Cited

U.S. PATENT DOCUMENTS 4,737,791 * 4/1988 Jean ........................................ 342/124
4,807,471 * 2/1989 Cournane ............................... 324/632
4,847,623 * 7/1989 Jean ........................................ 342/124

* cited by examiner

Primary Examiner—Safet Metjahic
Assistant Examiner—Anjan K Deb
(74) Attorney, Agent, or Firm—John MacEvoy

(57) ABSTRACT

This invention provides apparatus for and a method of locally or remotely monitoring a number of geophysical and other variables related to the refractive index of materials, e.g., soil and pavement moisture content; the moisture content of bulk food products such as grains and beans; liquid levels in storage tanks; interface levels between water and floating layers of oil; the thickness of ice layers; the water/ice interface in partially frozen ground; the location of liquid and gas leaks on roofs, in landfill liners, geosynthetic membranes, and pipelines; and the cables. The detection technique is based on the reflection of frequency-modulated continuous waves during their propagation along transmission line probes embedded in the material being tested.

13 Claims, 2 Drawing Sheets

TRANSMISSION LINE REFLECTOMETER USING FREQUENCY-MODULATED CONTINUOUS WAVE

GOVERNMENT INTEREST STATEMENT

The invention described herein may be manufactured, licensed, and used by or for governmental purposes without the payment of any royalties thereon.

I. BACKGROUND OF THE INVENTION

1. Field of the Invention

This invention relates to apparatus for and a method of monitoring a number of geophysical and other physical variables by way of the refractive index or, indirectly, the dielectric constant of materials. Specifically, it related to monitoring of such properties as soil and pavement moisture content; the moisture content of bulk food products such as grains and beans; liquid levels in storage tanks; interface levels between water and floating layers of oil or other petroleum products; the thickness of ice layers; the frozen/unfrozen interface in partially frozen ground; the location of liquid and gas leaks on roofs, in landfill liners, geosynthetic membranes, and pipelines; and the location of electrical short circuits, open circuits, and impedance discontinuities in cables. The detection technique is based on the reflection of frequency-modulated continuous waves during their propagation along transmission line probes embedded in the material being tested.

2. Prior Art

The frequency-modulated continuous wave technique has been used in radar system applications wherein electromagnetic waves are transmitted into space from antennas. Applications employing transmission lines have been disclosed in the inventor's previous application directed to the detection of water-sediment interfaces around bridge piers and pilings (Ser. No. 08965483, filed Nov. 6, 1997) and another application relating to the detection of frazil ice on underwater gratings (Ser. No. 08871624, filed Jun. 9, 1997).

II. SUMMARY OF INVENTION

This invention relates to apparatus for the monitoring, both locally and remotely, of physical variables related to the refractive index of materials such as moisture content, air/liquid interfaces, oil/water interfaces, and ice/water interfaces. It is applicable to measurements of soil and pavement moisture content, the moisture content of bulk food products, liquid levels in storage tanks, interface levels between water and floating layers of oil or other petroleum products, the thickness of ice layers, the frozen/unfrozen interface in partially frozen ground, the location of liquid and gas leaks on roofs, electrical short circuits, open circuits, and impedance discontinuities in cables.

The apparatus comprises a transmission line probe, inserted into the material being monitored, means for generating a frequency-modulated continuous voltage wave signal, means for detecting frequency differences between frequency-modulated voltage signals. The interpretation of frequency difference signals involves the solution of equations interrelating the refractive indices of materials the distance from the proximal end of the transmission line probe to the location of discontinuities in refractive index, and to the length of the probe.

In the frequency-modulated continuous wave method of this invention, a transmission line probe is inserted into the medium whose properties are being monitored and a frequency-modulated continuous wave is applied to the proximal end of the probe. The wave propagates along the transmission line probe at the speed equal to the speed of light divided by the refractive index. The refractive index is equal to the square root of the dielectric constant of the material in which the probe is embedded. Reflected waves will be generated at points along the probe where discontinuities in refractive index occur, and at the distal end of the probe.

The frequency of the continuous wave signal is modulated, i.e., the frequency is altered with respect to time. Preferably, the frequency increases or decreases linearly with time form a low frequency to a high frequency, the difference between these frequencies being referred to as bandwidth. Non-linear frequency modulation patterns may be used but linear variation of frequency with time is preferred.

Mixing the input wave signal with reflected wave signal produces frequency sum and frequency difference signals which are related to the distance traveled by the waves to a refractive index discontinuity, or to the end of the probe, and to the refractive indexes of the materials surrounding the probe. Frequency sum signal components are filtered out by a low-pass network; only frequency difference signal components are amplified and utilized. Refractive indices are empirically correlated with moisture content, ice content, liquid-liquid interface level, the location of liquid or gas leaks, and the location of electrical short circuits or breaks in electrical cables.

The frequency differences signals may be recorded locally or transmitted by wireless means to remote monitoring/data recording equipment.

III. BRIEF DESCRIPTION OF THE DRAWINGS

IV. PREFERRED EMBODIMENTS OF THE INVENTION

Figure 1:
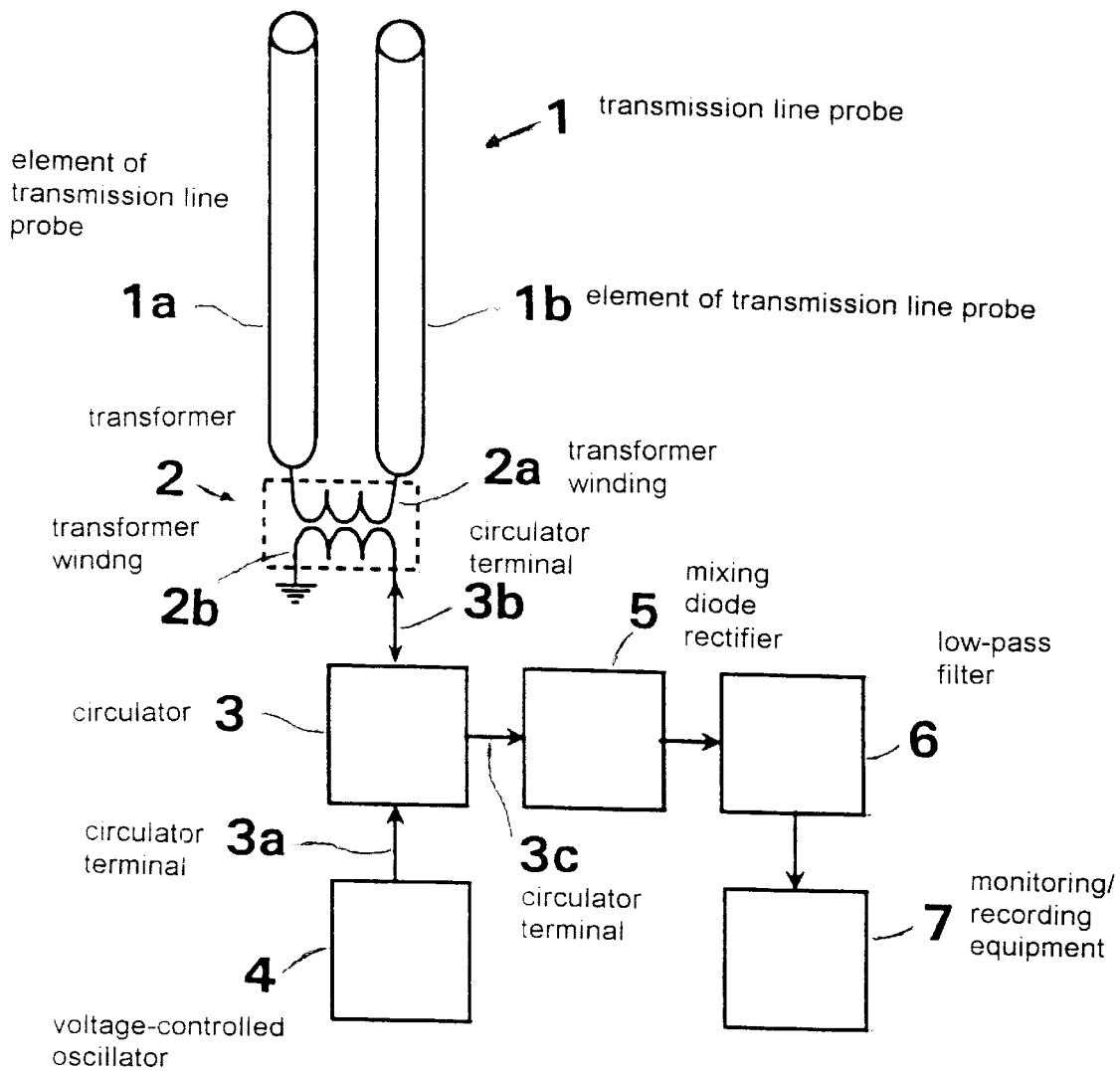
FIG. 1 is a schematic depiction of the elements of the frequency-modulated continuous wave monitoring system of this invention.

With reference to FIG. 1, a transmission line probe comprising two parallel elements 1a and 1b is connected to the secondary winding 2a of a transformer 2, whose primary winding 2b is connected to a terminal 3b of a circulator 3. The function of the transformer 2 is to match output and input impedances between the transmission line probe and the means for detecting frequency differences between frequency-modulated voltage signals, to ensure adequate signal transmission line probe may be directly connected to the means for frequency difference detection if the said output and input impedances are approximately matched.

An input terminal 3a of the circulator 3 connects to the output of a voltage-controlled oscillator 4 whose frequency is varied by a voltage sweep generator (not illustrated). Preferably, the voltage sweep generator produces a voltage that rises or falls linearly with time during a sweep interval, causing the voltage-controlled oscillator to generate an output signal whose frequency reset or falls linearly with time. Other, non-linear voltage sweep patterns may also be used, but linear sweep patterns are preferred.

The frequency-modulated signal at terminal 3a is transmitted by the circulator to its terminal 3b and thereby to the transformer primary 2b, the transformer secondary 2a, and the probe elements 1a and 1b through the transformer secondary 2a, the transformer primary 2b, the terminal 3b of the circulator 3, and via the circulator to its terminal 3c.

Figure 2:
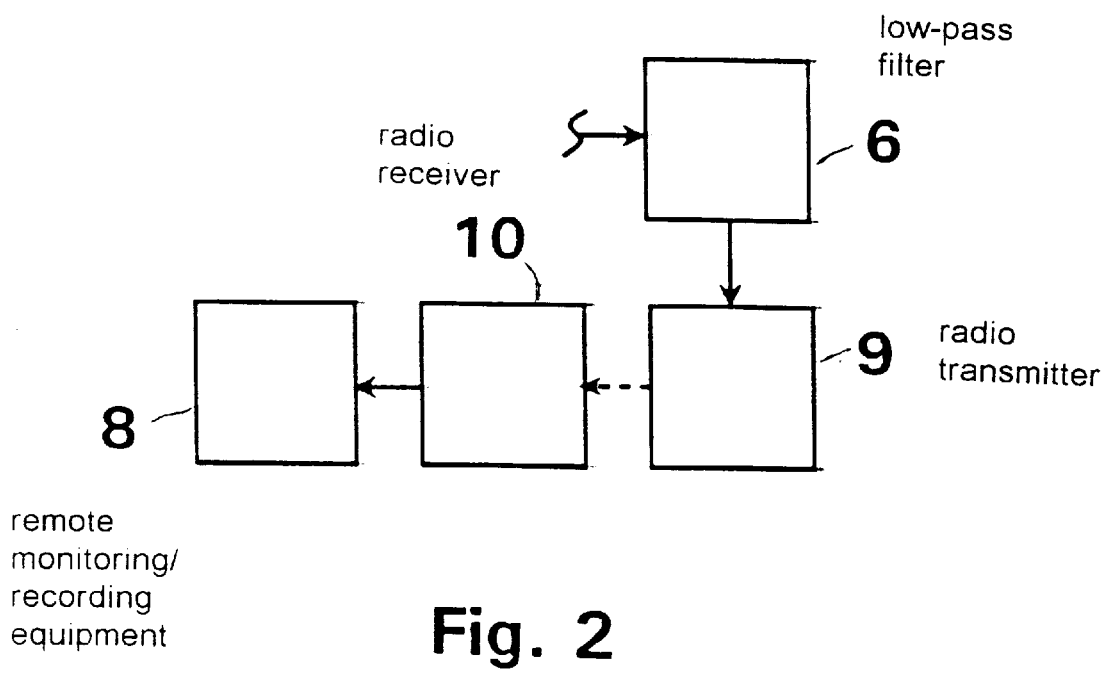
FIG. 2 illustrates an alternative embodiment of the invention.

The output terminal 3c of the circulator 3 connects to a diode mixer 5 followed by a low-pass filter 6. When frequency-modulated signals are sent into the transmission line probe elements 1a and 1b, the mixing of these signals and their reflections, both at refractive index discontinuities along the transmission line probe 1 as well as at the ends of the probe elements, produce frequency sum and differences signals at the input of the mixing diode rectifier 5. The rectified frequency sum signal components are filtered out in the low-pass filter 6; only the frequency difference signal components appear at the out put of the low-pass filter 6. These signals are amplified and fed to near-by monitoring/recording equipment 7 by hardwire connections or, as shown in FIG. 2, transmitted to remote monitoring/recording equipment 8 by a radio transmitter 9 and a radio receiver 10.

The circulator 3 is defined herein as a device that has three terminals, 3a, 3b, and 3c, as shown in FIG. 1, wherein a voltage signal applied to 3a passes to 3b, but not in the reverse direction. Circulators as here defined may be electronic devices using magnetic properties or devices referred to as "Ts", "hybrid-Ts", or "Magic-Ts." Alternatively, the three terminals 3a, 3b, and 3c may be connected to each other directly and the circulator 3 omitted.

The embodiments of this invention will be more fully described by the following examples.

EXAMPLE 1

In this example, the frequency-modulated continuous wave reset linearly from 10 $MH_z$ to 500 $MH_z$ over a 100 millisecond (0.1 sec) sweep interval $t_{swp}$. The bandwidth BW is 490 $MH_z$ (490×10$^6$ $H_z$).

The probe elements 1a and 1b are embedded in a sand pile whose moisture content is being monitored. Their length D is 30 cm (0.3 m). The refractive index n of dry sand is 1.58. The frequency difference signal at terminal 3b is $$F_D = 2 \times D \times BW \times n/t_{swp}/C = 15.5 \ H_z,$$

where c is the speed of light, 3×10$^8$ m/sec. This result is obtained in the above formula by multiplication of the rate of change of signal frequency, BW/$t_{swp}$, by the path length traveled by the signals along the probe and back, 2D, and division by the speed of signal travel, c/n.

Now the probe elements are embedded in a sand pile of unknown moisture content and the frequency difference received at terminal 3b is 45 $H_z$. Solving the above formula for the refractive index, $$n = F_D \times t_{swp} \times C/2/BW/D = 4.6.$$

This value of the refractive index corresponds to 22 volume percent water content in the wet sand as determined by experimental correlation between refractive index and moisture content, or as calculated from the dielectric constants of sand and water.

EXAMPLE 2

The probes elements are embedded in a sheet of ice floating on water, with the ends of the probe elements protruding into the water below the ice. The refractive index of ice n is 1.78, the initial frequency is 5 MHz, the final frequency is 300 MHz, the band width BW is 295 MHz (295×10$^6$ $H_z$), the sweep time interval $t_{swp}$ is 50 milliseconds (0.05 sec), and the observed frequency difference $F_D$ is 40 $H_z$. The thickness of he ice D is calculated from the formula $$D = F_D \times t_{swp} \times c/2/BW/n = 0.57 \ m = 57 \ cm$$

Here, the length l of the probe elements is irrelevant as long as their length exceeds the thickness of the ice layer. The frequency difference signal reflected from the end of the probe-elements also is irrelevant to this measurement and is ignored.

The transmission line probes of this invention may be exposed to wet and corrosive conditions in some applications. They may be made of relatively corrosion-resistant materials, e.g., stainless steel, galvanized iron, brass, or bronze. Alternatively, they may be made of carbon steel pipes, rods, or rebar covered by polymeric protective coatings such as primers and paint.

The dimensions of the elements of the probes of this invention vary greatly depending on the applications. The length may range from 15 cm to 2 m. Diameters may range from 1 to 50 mm. Spacing between parallel elements ranges from 5–20 cm center-to-center.

Ordinarily, the probes of this invention comprise two parallel elements. Optionally, several additional parallel elements may be employed. For example, one element is positioned centrally and a second and a third element are placed equidistantly and on opposite sides of the first element. Additional elements may be similarly placed around the first element.

The foregoing is considered as illustrative of the principles of this invention. Numerous modifications and changes may occur to those skilled in the art. It is not desired to limit the invention to the exact construction as shown and described. Accordingly, all suitable modifications fall within the scope of this invention.

What is claimed is:

1. Apparatus for the monitoring of physical variables of an interface between materials related to the refractive indices of such materials comprising a, a transmission line probe placed in the materials;

b, means for generating a frequency-modulated continuous voltage wave signal electrically connected to said probe and for passing said wave signal to the probe; and generating reflected wave signals at discontinuities in refractive indices of materials;

c, means in electrical communication with said probe for detecting the resulting frequency differences, and d, means, in electrical communication with said means for detecting frequency differences, for interpreting, recording, and storing said frequency differences, whereby the refractive indices of the interface between materials are measured.

2. Apparatus according to claim 1 wherein the transmission line probe comprises at least two elements mounted parallel to each other.

3. Apparatus according to claim 1 wherein the transmission line probe comprises a first element and a plurality of second elements mounted parallel to the first element and positioned equidistantly around the first element.

4. Apparatus according to claim 1 further comprising a transformer whose secondary windings are electrically connected to the probe and whose primary windings are electrically connected to the means for detecting frequency difference.

5. Apparatus according to claim 1 further comprising a circulator having a first terminal connected to the means of generating frequency-modulated signals, and a second terminal connected to the probe, and a third terminal connected to the means for detecting frequency differences.

6. Apparatus according to claim 1 wherein the means for generating a frequency-modulated signal is a voltage-controlled oscillator.

7. Apparatus according to claim 6 wherein the frequency of the signal varies linearly with time.

8. Apparatus according to claim 1 wherein the means for detecting frequency differences comprises a mixer diode and a low-pass filter, whereby frequency-modulated signals are rectified and wherein undesired high frequency components are filtered out.

9. Apparatus according to claim 1 wherein the means for interpreting, recording and storing frequency difference signals comprises and amplifier and monitoring and signal processing and recording equipment.

10. Apparatus according to claim 9 further comprising a radio transmitter and receiver, the transmitter connected to the amplifier and the receiver connected to the monitoring and recording equipment, whereby frequency difference signals are transmitted to the receiver and the monitoring and recording equipment at a remote location.

11. The apparatus of claim 1 wherein said interface between materials is between solid and liquid.

12. The apparatus of claim 1 wherein said interface between materials is between liquid and liquid.

13. A method for monitoring physical variables of an interface between materials related to the refractive indices of such materials comprising a, placing a transmission line probe within said materials;

b, generating a frequency-modulated continuous voltage wave signal and passing it to the probe; and causing a reflected voltage signal to be generated at said interface which marks discontinuities in refractive index of the materials;

c, mixing said reflected signal with the continuous voltage wave signal;

d, detecting frequency difference signals between the continuous voltage wave signal and the reflected signal and e, interpreting, recording, and storing said frequency differences, whereby the refractive indices of the interface between said materials are measured and the desired variables are calculated.

* * * * *